United States Patent [19]

Ife

[11] Patent Number: 4,532,246

[45] Date of Patent: Jul. 30, 1985

[54] 2-(2-PYRIDYLAMINOALKYLAMINO)-4-PYRIMIDONES

[75] Inventor: Robert J. Ife, Stevenage, England

[73] Assignee: Smith Kline & French Laboratories Limited, Welwyn Garden City, England

[21] Appl. No.: 563,496

[22] Filed: Dec. 20, 1983

[30] Foreign Application Priority Data

Dec. 23, 1982 [GB] United Kingdom ................. 8236637
Aug. 19, 1983 [GB] United Kingdom ................. 8322349

[51] Int. Cl.³ .................. A61K 31/505; A61K 31/44; C07D 239/02
[52] U.S. Cl. .................................... 514/275; 514/342; 514/335; 514/352; 544/320; 546/261; 546/277; 546/304
[58] Field of Search ......................... 544/320; 424/251

[56] References Cited

U.S. PATENT DOCUMENTS

| | | | |
|---|---|---|---|
| 3,535,328 | 10/1970 | Zielinski | 260/296 |
| 3,932,644 | 1/1976 | Durant et al. | 424/263 |
| 4,062,863 | 12/1977 | Ganellin et al. | 424/260 |
| 4,255,428 | 3/1981 | Brown et al. | 424/251 |
| 4,394,508 | 7/1983 | Crenshaw et al. | 424/250 |

Primary Examiner—Donald G. Daus
Assistant Examiner—Cecilia Shen
Attorney, Agent, or Firm—Joan S. Keps; Richard D. Foggio; Alan D. Lourie

[57] ABSTRACT

Pyridine derivatives are disclosed which are useful as histamine $H_1$-antagonists.

8 Claims, No Drawings

2-(2-PYRIDYLAMINOALKYLAMINO)-4-PYRIMIDONES

This invention relates to certain pyridine derivatives, a process for their preparation, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine.

According to the present invention there is provided compounds of formula (1):

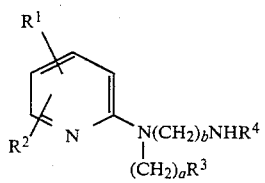

and pharmaceutically acceptable salts thereof, where
$R^1$ and $R^2$ are the same or different and are hydrogen, $C_{1-6}$ alkyl, $C_{1-6}$ alkoxy or halogen;
$R^3$ is optionally substituted phenyl or optionally substituted pyridyl, where the optional substituents are one or more $C_{1-6}$ alkyl, $C_{1-6}$ alkoxy, or hydroxy groups or halogen atoms; or optionally substituted thiazolyl, optionally substituted furanyl or optionally substituted thienyl where the optional substituents are one or more $C_{1-6}$ alkyl or $C_{1-6}$ alkoxy groups or halogen atoms;
a is from 1 to 6
b is from 2 to 4
and $R^4$ is a group of formula (2):

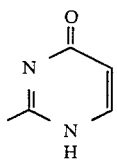

or a group of formula (3):

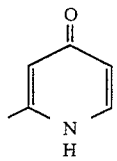

or a group of formula (4):

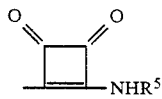

or a group of formula (5):

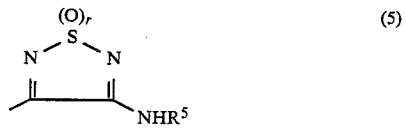

where $R^5$ is hydrogen, $C_{1-6}$ alkyl, or $(CH_2)_d R^6$ where d is 1–6 and $R^6$ is optionally substituted phenyl, optionally substituted pyridyl, where the optional substituent is one or more $C_{1-6}$ alkyl, $C_{1-6}$ alkoxy or hydroxy groups or halogen atoms; optionally substituted thiazolyl, optionally substituted furanyl or optionally substituted thienyl, where the optional substituents are one or more $C_{1-6}$ alkyl or $C_{1-6}$ alkoxy groups or halogen atoms; and r is 0 to 2.

The compounds of this invention are histamine $H_1$-antagonists and are useful for the treatment of diseases for example bronchial asthma, rhinitis, hayfever and allergic eczema whose symptoms are mediated through the action of histamine at $H_1$-receptors.

Examples of halogens for $R^1$, $R^2$ and the halogen substituent in $R^3$ and $R^6$ are fluorine, chlorine, bromine or iodine.

Examples of $C_{1-6}$ alkyl groups for $R^1$, $R^2$, $R^5$ and the $C_{1-6}$ alkyl substituent in $R^3$ and $R^6$ are methyl, ethyl, n-propyl, iso-propyl, n-butyl and t-butyl.

Examples of $C_{1-6}$ alkoxy groups for $R^1$, $R^2$ and the $C_{1-6}$ alkoxy substituents in $R^3$ and $R^6$ are methoxy, ethoxy, n-propoxy and n-butoxy.

Preferably $R^1$ and $R^2$ are both hydrogen.

By way of example, a can be 1, 2 or 3. Preferably it is 1.

By way of example, b can be 2, 3 or 4. Preferably it is 3.

Examples of substituted phenyl groups for $R^3$ and $R^6$ are 2-methylphenyl, 2-methoxyphenyl, 2-chlorophenyl, 2-fluorophenyl, 3-methylphenyl, 3-methoxyphenyl, 3-chlorophenyl, 3-fluorophenyl, 4-methylphenyl, 4-methoxyphenyl, 4-chlorophenyl and 4-fluorophenyl.

Examples of optionally substituted pyridyl groups for $R^3$ and $R^6$ are optionally substituted 2-pyridyl, 3-pyridyl, or 4-pyridyl groups.

Where $R^3$ or $R^6$ is thiazolyl, it can be 2-, 4- or 5-thiazolyl. In particular it is 2-thiazolyl.

Examples of optionally substituted furanyl groups for $R^3$ and $R^6$ are 2-furanyl and 3-furanyl.

Examples of optionally substituted thienyl groups for $R^3$ and $R^6$ are 2-thienyl and 3-thienyl.

In particular, a is 1 and $R^3$ is phenyl, 2-chlorophenyl, 2-fluorophenyl, 3-chlorophenyl, 3-fluorophenyl, 4-chlorophenyl, 4-fluorophenyl, 2-thienyl, 3-thienyl, 2-furanyl, 2-thiazolyl, 2-pyridyl, 3-pyridyl or 4-pyridyl.

Preferably $R^3$ is phenyl, 4-fluorophenyl, 2-thienyl or 3-thienyl.

When $R^4$ is a group of formula (4) or (5), $R^5$ is in particular, hydrogen, methyl or —$(CH_2)_d R^6$ where d is 1 and $R^6$ is 2-pyridyl, 3-pyridyl or 4-pyridyl. Preferably $R^4$ is a group of formula (5) and $R^5$ is preferably hydrogen or methyl, or —$(CH_2)_d R^6$ where d is 1 and $R^6$ is 3-pyridyl or 4-pyridyl.

When $R^4$ is a group of formula (5), r is in particular 1 or 2.

Compounds of formula (1) form pharmaceutically acceptable salts with pharmaceutically acceptable acid addition salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

Compounds of formula (1) where $R^4$ is a group of formula (2) or (3) can be prepared by reacting an amine of formula (6):

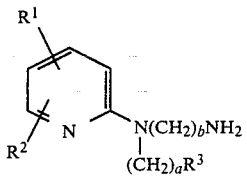

where $R^1$, $R^2$, $R^3$, a and b are as defined with reference to formula (1) with a compound of formula (7) or (8):

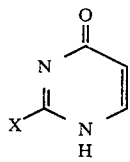

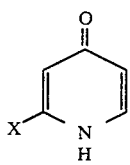

where X is a group displaceable with an amine.

Compounds of formula (1) where $R^4$ is a group of formula (4) or (5) can be made by reacting an amine of formula (6) above with a compound of formula (9) or (10):

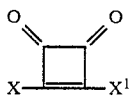

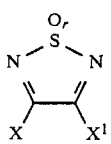

where X is as previously defined and $X^1$ is a group displaceable with an amine or a group of formula $NHR^5$ where $R^5$ is as previously defined, and where $X^1$ is a group displaceable with an amine, thereafter reacting with an amine of formula (12):

$R^5NH_2$      (12)

where $R^5$ is as defined with reference to formula (1).

Examples of leaving groups displaceable by amines are where X and $X^1$ are QS—, QSO—, $QSO_2$—, or QO— (Q being $C_{1-6}$ alkyl, aryl or aralkyl) halogen, particularly chlorine and bromine, and nitroamino. For compounds of formula (7), X is preferably nitroamino or QS where Q is methyl. For compounds of formula (8), preferably X is halogen. For compounds of formula (9) or (10), preferably the groups X and $X^1$ are QO— where Q is methyl.

The conditions under which the reaction is carried out depends upon the nature of the reagents. For example for compounds of formulae (7) and (8) and formula (9) where $X^1$ is $NHR^5$, the reaction can be carried out at an elevated temperature in the absence of a solvent, for example at from 80° to 170° C., preferably from 120° to 140° C., or in a solvent at an elevated temperature, for example at the reflux temperature of the reaction mixture. For compounds of formula (9) where $X^1$ is a group displaceable by an amine and for compounds of formula (10), the reaction is carried out at moderate to low temperature e.g. from 0° C. to room temperature. The choice of solvent is affected by the solubility characteristics of the reagents. Preferably the solvent is pyridine, a picoline or mixture of picolines, a $C_{1-6}$ alkanol, preferably ethanol or 1-propanol, 1,2-ethanediol, a high boiling alkoxyaryl ether for example anisole, or a polar aprotic solvent, for example dimethylformamide, dimethylacetamide, dimethylsulphoxide, hexamethylphosphoramide or sulpholane.

Pharmaceutically acceptable salts of compounds of formula (1) can be prepared by standard methods, for example by reacting a solution of the compound of formula (1) with a solution of the acid.

Compounds of formula (6) can be prepared by reacting a compound of formula (11):

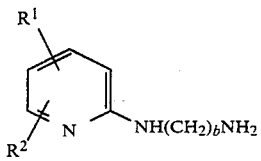

where $R^1$ and $R^2$ and b are as defined with reference to formula (1) or a derivative thereof where the primary amino group is protected, with a compound of formula (11a):

$R^3(CH_2)_aX^2$      (11a)

where $R^3$ and a are as defined with reference to formula (1) (provided that any hydroxy groups in $R^3$ are protected) and $X^2$ is halogen, in the presence of a strong base and thereafter removing any protecting groups.

Compounds of formula (11) can be prepared in turn by reacting a compound of formula (13):

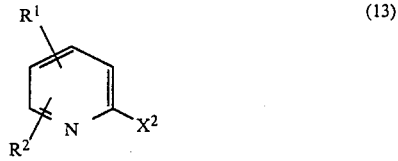

where $R^1$ and $R^2$ are as defined with reference to formula (1) and $X^2$ is halogen with an amine of formula (14):

$NH_2(CH_2)_bNH_2$      (14)

Compounds of formula (6) can also be prepared by reacting a compound of formula (15):

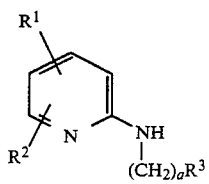

(15)

where $R^1$, $R^2$, $R^3$ and a are as defined with reference to formula (1) (provided that any hydroxy groups in $R^3$ are protected) with a compound of formula (16):

where b is as defined with reference to formula (1), $X^2$ is halogen and $R^5$ is a protected amino group, in the presence of a strong base and thereafter removing any protecting groups.

Examples of hydroxy protecting groups are $C_{1-6}$ alkyl, for example methyl, and $C_{1-6}$ alkanoyl, for example formyl or acetyl.

These protecting groups can be removed by standard methods, in particular under basic conditions.

Examples of protected amino groups for $R^5$ include phthalimido. In formulae (11a), (13) and (16) $X^2$ can be chlorine, bromine or iodine.

Examples of strong bases are alkali metal hydrides, particularly sodium hydride. The reaction is carried out in the presence of a polar solvent for example dimethylsulphoxide.

The protected amino group can be converted into amino by standard methods, for example when it is phthalimido by reaction with hydrazine.

The use of protecting groups is discussed in J. F. McOmie, Protective Groups in Organic Chemistry, 1973, Plenum Press, IBSN 0-306-30717-0.

Compounds of formulae (9) and (10) are known or can be made by known methods as described in for example U.K. Pat. No. 1,563,090 and U.K. Patent Application No. 2067987A.

Compounds of formulae (7), (8), (11a), and (12) to (16) are known or can be made by known methods.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of the Examples have $pA_2$ values greater than 7.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (2) or a pharmaceutically acceptable salt thereof and a pharmaceutically acceptable carrier.

Compounds of formula (2) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier of parenterally acceptable oil.

Compounds of formula (2) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol.

Where appropriate, bronchodilators and antiasthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included.

Each dosage unit for oral administration contains preferably from 1 to 200 mg of a compound of formula (2) or a pharmaceutically acceptable salt thereof calculated as the free base.

A dosage unit for parenteral administration contains preferably from 1 to 10 mg of a compound of formula (2) or a pharmaceutically acceptable salt thereof calculated as the free base.

The invention also provides a method of blocking histamine $H_1$-receptors which comprises administering to a subject an effective amount to block said receptors of a compound of formula (2) or a pharmaceutically acceptable salt thereof.

The compounds of formula (2) and their pharmaceutically acceptable salts will normally be administered to a subject in a pharmaceutical composition as described above, for the treatment of rhinitis, hayfever, bronchial asthma or allergic eczema. Typically the daily dosage regimen for an adult patient is between 15 mg and 400 mg and preferably between 15 mg and 200 mg or an intravenous, subcutaneous or intramuscular dose of between 1 mg and 50 mg, and preferably between 1 mg and 10 mg of a compound of formula (2) or a pharmaceutically acceptable salt thereof calculated as the free base, the composition being administered 1 to 4 times per day.

The following Examples illustrate the invention.

EXAMPLE 1

(i) 2-Bromopyridine (20 g), 1,3-diaminopropane (47 g) and pyridine (13 ml) were heated together under reflux for 2.5 hr. The mixture was evaporated to remove the excess of diaminopropane and the residue taken up in water. The pH was adjusted to 14 and extracted with chloroform. The extracts were dried ($K_2CO_3$) and the solvent was evaporated. The residue was distilled at reduced pressure to give 2-(3-aminopropylamino)pyridine, (13.3 g; 70%) b.p. 90°–91° C., 0.02 mm Hg.

(ii) A mixture of sodium hydride (0.7 g) and 2-(3-aminopropylamino)pyridine (4.02 g) in dimethylsulphoxide (25 ml) was heated slowly to 75° C. under nitrogen. After the evolution of hydrogen had ceased the solution was cooled to room temperature and benzyl bromide (3.17 ml) added dropwise below 35° C. After a further 30 minutes water was added and the mixture extracted with chloroform. The chloroform extracts were washed with 2N hydrochloric acid, the pH of the aqueous layers adjusted to 4.5 and re-extracted with chloroform. The pH was further raised to 14 and again extracted with chloroform. The final chloroform extract was dried ($K_2CO_3$) and the chloroform was evaporated to give 2-[N-(3-aminopropyl)-N-benzylamino]pyridine as an oil (3.91 g) which was used without further purification.

(iii) 2-[N-(3-Aminopropyl)-N-benzylamino]pyridine (1.07 g) and S-methyl-2-thiouracil (2 g) were fused together on an oil bath at 130°–60° C. for 4.5 hr. On cooling the residue was chromatographed (silica gel, ammoniacal methanol/chloroform 1:25). The solvent was evaporated from the fractions containing the required product and the residue recrystallised from ethanol to give 2-[3-(N-benzyl-N-(2-pyridyl)amino)propylamino]-pyrimid-4-one, (1.0 g; 68%) m.p. 162°–3° C.

$C_{19}H_{21}N_5O$: Found: C, 68.08; H, 6.51; N, 20.87. Requires: C, 68.04; H, 6.31; N, 20.88%.

EXAMPLE 2

(i) Sodium hydride (1.32 g) was dissolved in dimethylsulphoxide (25 ml) at 70°–75° C. under nitrogen. The solution was cooled and 2-(3-aminopropylamino)pyridine (7.56 g) in dimethylsulphoxide (20 ml) added at room temperature. 3-Chlorobenzyl chloride (8.86 g) in dimethylsulphoxide (15 ml) was added dropwise maintaining the temperature at 20°–25° C. After a further 1 hour, water was added (200 ml) and the mixture extracted with ether. The ether extracts were washed with 2N hydrochloric acid and the aqueous layer adjusted to pH 3.5. After extracting with chloroform the pH was raised to 14 and extracted with ether. After drying ($K_2CO_3$), the final ether extracts were evaporated to give 2-[N-(3-aminopropyl)-N-(3-chlorobenzyl)amino]pyridine (8.34 g) as an oil which was used without further purification.

(ii) 2-[N-(3-Aminopropyl)-N-(3-chlorobenzyl)amino]pyridine (2.11 g) and S-methyl-2-thiouracil (0.91 g) were fused together on an oil bath at 160° C. for 3 hr. On cooling the residue was crystallised from ethanol/water and then chromatographed (silical gel, 1% methanol/chloroform). The solvent was evaporated from the fractions containing the required product and the residue crystallised from ethanol/water to give 2-[3-[N-(3-chlorobenzyl)-N-(2-pyridyl)amino]propylamino]-pyrimid-4-one 0.7 $H_2O$, (0.89 g; 36%) m.p. 74°–8° C.

$C_{19}H_{20}ClN_5O$ 0.7 $H_2O$: Found: C, 59.54; H, 5.57; N, 18.58; Cl, 9.32. Requires: C, 59.66; H, 5.64; N, 18.31; Cl, 9.27%.

EXAMPLE 3

(i) A mixture of sodium hydride (1.12 g) and 2-(3-amino-propylamino)pyridine (7.05 g) in dimethylsulphoxide (30 ml) was heated slowly to 85° C. under nitrogen. After the evolution of hydrogen had ceased the solution was cooled to room temperature and 4-chlorobenzyl chloride (5.95 ml) in dimethylsulphoxide (10 ml) added dropwise keeping the temperature below 30° C. After standing for 72 hr, water (300 ml) was added and the mixture extracted with ether. The extract was washed with water and 2N hydrochloric acid. The pH of the acid washing was raised to 6 and extracted with ether. The pH was raised further to 14 and extracted again with ether. The ether extract was dried ($MgSO_4$) and the ether evaporated to give 2-[N-(3-aminopropyl)-N-(4-chlorobenzyl)amino]pyridine (7.43 g) as an oil, b.p. 160° C. 0.04 mm Hg.

(ii) 2-[N-(3-Aminopropyl)-N-(4-chlorobenzyl)amino]pyridine (2.11 g) and S-methyl-2-thiouracil (0.91 g) were heated together under reflux in pyridine (5 ml) for 24 hr. On cooling, the solvent was evaporated. The residue was triturated with ether and recrystallised from ethanol to give 2-[3-[N-(4-chlorobenzyl)-N-(2-pyridyl)amino]propylamino]pyrimid-4-one 0.2 $H_2O$, 1.55 g (65%) m.p. 168°–70° C.

$C_{19}H_{20}ClN_5O$ 0.2 $H_2O$: Found: C, 61.45; H, 5.62; N, 18.47; Cl, 9.30. Requires: C, 61.11; H, 5.51; N, 18.75; Cl, 9.49%.

EXAMPLE 4

(i) A mixture of sodium hydride (0.95 g) and 2-(3-aminopropylamino)pyridine (5.4 g) in dimethylsulphoxide (25 ml) was heated slowly to 85° C. under nitrogen. After the evolution of hydrogen had ceased the solution was cooled to room temperature and 4-methoxybenzyl chloride (5.59 g) in dimethylsulphoxide (5 ml) added dropwise keeping the temperature below 30° C. After a further 1 hr, water (300 ml) was added and the mixture extracted with ether. The extract was washed with 2N hydrochloric acid. The pH of the acid washings was adjusted to 4–5. After extracting with chloroform the pH was raised to 14 and extracted with ether. The ether extract was washed with water, dried ($K_2CO_3$) and the ether evaporated to give 2-[N-(3-aminopropyl)-N-(4-methoxybenzyl)amino]pyridine (7.19 g) as an oil which was used without further purification.

(ii) 2-[N-(3-Aminopropyl)-N-(4-methoxybenzyl)amino]pyridine (1.63 g) and 2-methyl-2-thiouracil (0.71 g) were heated together under reflux in pyridine (5 ml) for 20 hr. On cooling, the solvent was evaporated. The residue was triturated with wet ether and recrystallised three times from isopropanol/water to give 2-[3-[N-(4-methoxybenzyl)N-(2-pyridyl)amino]propylamino]-pyrimid-4-one 0.25 $H_2O$, (0.91 g; 49%) m.p. 63°–80° C.

$C_{20}H_{23}N_5O_2$ 0.25 $H_2O$: Found: C, 64.74; H, 6.29; N, 18.78. Requires: C, 64.93; H, 6.40; N, 18.93%.

EXAMPLE 5

(i) Sodium hydride (1.32 g) was dissolved in dimethylsulphoxide (25 ml) at 70°–75° C. under nitrogen. The solution was cooled and 2-(3-aminopropylamino)pyridine (7.5 g) added at room temperature. 2-Chlorobenzyl chloride (8.86 g) in dimethylsulphoxide (15 ml) was added dropwise maintaining the temperature at 20°–25° C. After standing overnight water (200 ml) was added and the mixture extracted with ether. The ether extracts were washed with 2N hydrochloric acid and after partitioning into ether and chloroform at pH 3.5 and 14 an oil was obtained which was further purified by HPLC (silica gel, dichloromethane then 2% ammoniacal methanol/dichloromethane) to give 2-[N-(3-aminopropyl)-N-(2-chlorobenzyl)amino]pyridine (3.44 g) as an oil.

(ii) 2-[N-(3-Aminopropyl)-N-(2-chlorobenzyl)amino]pyridine (1 g) and S-methyl-2-thiouracil (0.43 g) were heated together under reflux in pyridine (5 ml) for 20 hr. After evaporating the solvent, the residue was triturated with ether and recrystallised twice from ethanol/water to give 2-[3-[N-(2-chlorobenzyl)-N-(2-pyridyl)amino]propylamino]pyrimid-4-one 0.5 $H_2O$ (0.72 g; 54%), m.p. 153°–54° C.

$C_{19}H_{20}ClN_5O$ 0.5 $H_2O$: Found: C, 60.45; H, 5.34; N, 18.22; Cl, 9.55. Requires: C, 60.23; H, 5.59; N, 18.49, Cl, 9.36%.

EXAMPLE 6

(i) 2-Bromopyridine (15.8 g), ethylene diamine (30 g) and pyridine (10 ml) were heated together under reflux for 3 hr. The excess of ethylene diamine was evaporated at reduced pressure and the residue taken up in water. The pH was adjusted to 14 and extracted with chloroform. The extracts were dried ($K_2CO_3$), the solvent evaporated and the residue distilled at reduced pressure to give 2-(2-aminoethylamino)pyridine, (8.24 g; 60%) b.p. 80° C., 0.01 mm Hg.

(ii) A mixture of sodium hydride (0.53 g) and 2-(aminoethylamino)pyridine (2.74 g) in dimethylsulphoxide (30 ml) was heated slowly to 85° C. under nitrogen. After the evolution of hydrogen had ceased the solution was cooled to room temperature and benzyl bromide (2.37 ml) added dropwise keeping the temperature below 30° C. After a further 1 hr, water (200 ml) was added, the mixture extracted with ether and the extract washed with 2N hydrochloric acid. The pH of the aqueous layer was adjusted to 4.5 and extracted with chloroform. The pH was further raised to 14 and extracted with ether. The final ether extract was dried ($K_2CO_3$) and the ether evaporated to give 2-[N-(2-aminoethyl)-N-benzylamino]pyridine (2.58 g) as an oil which was used without further purification.

(iii) 2-[N-(2-Aminoethyl)-N-benzylamino]pyridine (1 g) and S-methyl-2-thiouracil (0.52 g) were fused together on an oil bath at 160° C. for 3 hr. On cooling the residue was triturated with ethanol and after chromatography (silica gel, 1% methanol/chloroform) and crystallisation from ethanol, gave 2-[2-(N-benzyl-N-(2-pyridyl)amino)ethylamino]pyrimid-4-one, (0.46 g; 37%), m.p. 187°–90° C.

$C_{18}H_{19}N_5O$ 0.25 $C_2H_5OH$: Found: C, 66.58; H, 6.10; N, 21.16. Requires: C, 66.74; H, 6.21; N, 21.04%.

EXAMPLE 7

To a stirred suspension of 3,4-dimethoxy-1,2,5-thiadiazole-1-oxide (1.34 g) in methanol (45 ml) at 5° C. was added dropwise over 30 min 2-[N-(3-aminopropyl)-N-benzylamino]pyridine (2.0 g) in methanol (15 ml). After a further 2 hr. at 5°–10° C., anhydrous ammonia was passed through the solution at 5° C. for 25 min. The mixture was then stirred for a further 2 hr. at room temperature. After evaporating the solvent, the residue was crystallised from ethanol to give 3-[3-(N-benzyl-N-(2-pyridyl)amino)propylamino]-4-amino-1,2,5-thiadiazole-1-oxide 0.2 $H_2O$, (1.29 g; 42%), m.p. 176°–78° C. (dec).

$C_{17}H_{20}N_6OS$ 0.2 $H_2O$: Found: C, 56.90; H, 5.69; N, 23.08; S, 8.63. Requires: C, 56.71; H, 5.71; N, 23.34; S, 8.91%.

EXAMPLE 8

(i) 2-Bromopyridine (10 g), 1,4-diaminobutane (35 ml) and pyridine (7 ml) were heated together under reflux for 4 hr. The excess of diaminobutane was evaporated and the residue taken up in water. The solution was extracted with chloroform at pH 7 and 13. This last extract was dried ($K_2CO_3$), the solvent evaporated and the residue was distilled at reduced pressure to give 2-(4-aminobutylamino)pyridine, (7.0 g; 67%) b.p. 136°–38° C., 2 mm Hg.

(ii) Sodium hydride (1.6 g) was dissolved in dimethylsulphoxide (35 ml) at 70°–75° C. under nitrogen. The solution was cooled and 2-(4-aminobutylamino)pyridine (10 g) in dimethylsulphoxide (10 ml) added at room temperature. Benzyl bromide (10.35 g) in dimethylsulphoxide (10 ml) was added dropwise maintaining the temperature at 25°–30° C. After a further 2 hr water (200 ml) was added and the mixture extracted with chloroform. The chloroform extract was washed with 2N hydrochloric acid and the aqueous layer basified to pH 4. After extracting with chloroform the pH was raised to 14 and again extracted with chloroform. The solvent was evaporated from the second chloroform extract. The residue was taken up in ether and the solution was washed with water. The ether layer was dried (K$_2$CO$_3$) and the ether evaporated to give 2-[N-(4-aminobutyl)-N-benzylamino]pyridine (5.61 g) as an oil which was used without further purification.

(iii) To a stirred suspension of 3,4-dimethoxy-1,2,5-thiadiazole-1-oxide (0.95 g) in methanol (40 ml) at 5° C. was added dropwise over 30 min 2-[N-(4-aminobutyl)-N-benzylamino]pyridine (1.5 g) in methanol (15 ml). After a further 2.5 hr at 5°–10° C., anhydrous ammonia was passed through the solution at 5° C. for 30 min. The mixture was then stirred for a further 2 hr. at room temperature and the solvent was then evaporated. The residue was chromatographed (silica gel, dichloromethane/methanol, 25:1) and the solvent was evaporated from the fractions containing the required product. The residue was crystallised from ethanol/water to give 3-[4-(N-benzyl-N-(2-pyridyl)amino)butylamino)-4-amino-1,2,5-thiadiazole-1-oxide 0.25 H$_2$O, (1.1 g; 51%), m.p. 134°–36° C.

C$_{18}$H$_{22}$N$_6$OS.0.25 H$_2$O: Found: C, 57.64; H, 6.05; N, 22.28; S, 8.57. Requires: C, 57.65; H, 6.05; N, 22.41; S, 8.55%.

EXAMPLE 9

To a stirred suspension of 3,4-dimethoxy-1,2,5-thiadiazole-1-oxide (0.88 g) in methanol (35 ml) at 5° C. was added dropwise over 35 min 2-[N-(3-aminopropyl)-N-(4-chlorobenzyl)amino]pyridine (1.5 g) in methanol (15 ml). After a further 2 hr at 5°–10° C., anhydrous ammonia was passed through the solution at 5° C. for 30 min. The mixture was then stirred for a further 2 hr. at room temperature. After evaporating the solvent the residue was chromatographed (silica gel, dichloromethane/methanol, 25:1). The solvent was evaporated from the fractions containing the required product to give 3-[3-[N-(4-chlorobenzyl)-N-(2-pyridyl)amino]-propylamino]-4-amino-1,2,5-thiadazole-1-oxide 0.2 H$_2$O, as a glass, (0.61 g; 29%) m.p. indeterminate.

C$_{17}$H$_{19}$ClN$_6$OS.0.2H$_2$O, 0.1 C$_2$H$_5$OH: Found: C, 51.67; H, 4.98; N, 21.03; S, 7.96; Cl, 9.09. Requires: C, 51.76; H, 5.06; N, 21.03; S, 8.02; Cl, 8.87%.

EXAMPLE 10

(i) Substituting p-chlorobenzyl chloride (19.49 g) for benzyl bromide and using corresponding molar proportions of the other reagents in the method of Example 8 (ii) gave 2-[N-(4-aminobutyl)-N-(4-chlorobenzyl)amino]pyridine (9.1 g) as an oil which was used without further purification.

(ii) Substituting 2-[N-(4-aminobutyl)-N-(4-chlorobenzyl)amino]pyridine (1.5 g) for 2-[N-(4-aminobutyl)-N-benzylamino]pyridine and using similar molar proportions of the other reagents in the method of Example 8 (iii) gave 3-[4-[N-(4-chlorobenzyl)-N-(2-pyridyl)amino]butylamino] -4-amino-1,2,5-thiadiazole-1-oxide, 0.9 g (43%) m.p. 175°–77° C. (from ethanol/water).

C$_{18}$H$_{21}$ClN$_6$OS: Found: C, 53.46; H, 5.27; N, 20.69; S, 7.96; Cl, 8.48. Requires: C, 53.39; H, 5.23; N, 20.76; S, 7.92; Cl, 8.76%.

EXAMPLE 11

To a stirred suspension of 3,4-dimethoxy-1,2,5-thiadiazole-1,1-dioxide (1.0 g) in methanol (100 ml) at 0°–5° C. was added dropwise over 1 hr 2-[N-(3-aminopropyl)-N-benzylamino]pyridine (1.35 g) in methanol (25 ml). After a further 2 hr. at 0°–10° C., anhydrous ammonia was passed through the solution at 0°–10° C. for 30 min. After standing overnight at room temperature the solvent was evaporated and the residue chromatographed (silica gel, chloroform/methanol, 25:1). The solvent was evaporated from the fractions containing the required product and the residue crystallised from ethyl acetate to give 3-[3-(N-benzyl-N-(2-pyridyl)amino)propylamino]-4-amino-1,2,5-thiadiazole-1,1-dioxide, (0.67 g; 32%), m.p. 192°–3° C.

C$_{17}$H$_{20}$N$_6$O$_2$S: Found: C, 55.06; H, 5.45; N, 22.41; S, 8.62. Requires: C, 54.82; H, 5.41; N, 22.57; S, 8.61%.

EXAMPLE 12

1-Amino-2-methoxycyclobutene-3,4-dione (0.22 g) and 2-[N-(3-aminopropyl)-N-benzylamino]pyridine (0.42 g) were dissolved in the minimum amount of dry pyridine and heated on an oil bath at 65° C. for 4 hr. On cooling, a white solid was obtained which was recrystallised from isopropanol and again from ethanol/water to give 1-amino-2-[3-(N-benzyl-N-(2-pyridyl)amino)propylamino]cyclobutene-3,4-dione, (0.22 g; 39%), m.p. 228°–31° C.

C$_{19}$H$_{20}$N$_4$O$_2$: Found: C, 63.85; H, 5.30; N, 16.18; S, 7.62. Requires: C, 63.72; H, 5.35; N, 16.16; S, 7.40%.

EXAMPLE 13

(i) Sodium hydride (1.74 g) was dissolved in dimethylsulphoxide (35 ml) at 70° C. under nitrogen. The solution was cooled and 2-(3-aminopropylamino)pyridine (10 g) in dimethylsulphoxide (10 ml) added at room temperature. 4-Fluorobenzyl bromide (12.5 g) in dimethylsulphoxide (10 ml) was added dropwise maintaining the temperature below 30° C. After a further 1.5 hr at room temperature water (100 ml) was added and the mixture extracted with chloroform. The extract was washed with 2N hydrochloric acid and the pH of the aqueous phase raised to 5.5. After re-extracting with chloroform the pH was raised to 14 and the aqueous phase extracted with ether. After drying (K$_2$CO$_3$), the ether extract was evaporated to give 2-[N-(3-aminopropyl)-N-(4-fluorobenzyl)amino]pyridine (7.48 g) as an oil which was used without further purification.

(ii) To a stirred suspension of 3,4-dimethoxy-1,2,5-thiadiazole-1-oxide (0.63 g) in methanol (35 ml) at 5° C. was added dropwise over 30 min 2-[N-(3-aminopropyl)-N-(4-fluorobenzyl)amino]pyridine (1 g) in methanol (35 ml). After 3 hrs at 5°–10° C., anhydrous ammonia was passed through the solution at 5°–10° C. for 1 hr. After a further 1 hr at 5°–10° C., the solvent was evaporated and the residue chromatographed (silica gel, chloroform/methanol, 6:1) to give 3-[3-[N-(4-fluorobenzyl)-N-(2-pyridyl)amino]propylamino]-4-amino-1,2,5-thiadiazole-1-oxide, (1.02 g; 70%) as a glass, m.p. indeterminate.

C$_{17}$H$_{19}$FN$_6$OS 0.37 H$_2$O: Found: C, 53.66; H, 5.16; N, 21.87; S, 8.61. Requires: C, 53.60; H, 5.18; N, 22.05; S, 8.41%.

EXAMPLE 14

2-[N-(3-Aminopropyl)-N-(4-fluorobenzyl)amino]-pyridine (1 g) in methanol (20 ml) was added dropwise to a stirred solution of 3,4-dimethoxy-1,2,5-thiadiazole-1-oxide in methanol (70 ml) at 5° C. After 3 hr the temperature was allowed to rise to 20° C. and a solution of methylamine in methanol (33% w/w, 2.1 ml) was added. The mixture was allowed to stand overnight and then evaporated to dryness. The residue was chromatographed (silica gel, chloroform/methanol, 20:1) to give, after crystallisation from acetone/water, 3-[3-[N-(4- fluorobenzyl)-N-(2-pyridyl)amino]propylamino]-4-methylamino-1,2,5-thiadiazole-1-oxide 1 H₂O, (1.31 g; 83%) m.p. 95°–105° C.

$C_{18}H_{21}FN_6OS$ 1 $H_2O$: Found: C, 53.19; H, 5.75; N, 20.53; S, 8.06. Requires: C, 53.18; H, 5.70; N, 20.67; S, 7.88%.

EXAMPLE 15

(i) Sodium hydride (1.1 g) was dissolved in dimethylsulphoxide (25 ml) at 70°–75° C. under nitrogen. The solution was cooled to room temperature and 2-(3-aminopropylamino)pyridine (6.22 g) in dimethylsulphoxide (10 ml) added dropwise with stirring. After 5 min, 2-chloromethylthiophene (6 g) in dimethylsulphoxide (10 ml) was added dropwise maintaining the temperature between 25°–35° C. After a further 1.5 hr, water (100 ml) was added and the mixture extracted with chloroform. The extract was washed with 2N hydrochloric acid and the pH of the aqueous phase raised to 4. After extracting with chloroform, the pH was raised further to 14 and extracted with ether. The ether extract was washed with dilute sodium hydroxide solution and dried (K₂CO₃). The ether extract was evaporated to give 2-[N-(3-aminopropyl)-N-(2-thienylmethyl)amino]pyridine (6.7 g) as an oil which was used without further purification.

(ii) To a stirred suspension of 3,4-dimethoxy-1,2,5-thiadiazole-1-oxide (1.62 g) in methanol (60 ml) at 5° C. was added dropwise over 45 min, 2-[N-(3-aminopropyl)-N-(2-thienylmethyl)amino]pyridine (2.47 g) in methanol (25 ml). After 2 hr at 5° C., anhydrous ammonia was passed through the solution for 30 min and the mixture allowed to stand overnight. The solvent was evaporated and the residue treated with ethanol to give a white solid which, after chromatography, (silica gel, chloroform/methanol 20:1) and trituration with ethanol gave 3-[3-(N-(2-thienylmethyl)-N-(2-pyridyl)amino)propylamino]-4-amino-1,2,5-thiadiazole-1-oxide (1.46 g; 40%) m.p. 169°–71° C.

$C_{15}H_{18}N_6OS_2$ 0.05$C_2H_5OH$: Found: C, 49.67; H, 5.01; N, 22.86; S, 17.74. Requires: C, 49.72; H, 5.06; N, 23.04; S, 17.58%.

EXAMPLE 16

2-[N-(3-Aminopropyl)-N-(2-thienylmethyl)amino]pyridine (2.47 g) in methanol (25 ml) was added dropwise to a stirred suspension of 3,4-dimethoxy-1,2,5-thiadiazole-1-oxide (1.62 g) in methanol (60 ml) at 5° C. After 2 hr a solution of methylamine in ethanol (33% w/w, 5 ml) was added and after a further 1 hr at 0°–10° C. the mixture was allowed to stand overnight at room temperature. The solvent was evaporated and the residue chromatographed (silica gel, chloroform/methanol 20:1) to give, after crystallisation from ethanol, 3-[3-(N-(2-thienylmethyl)-N-(2-pyridyl)amino)propylamino]-4-methylamino-1,2,5-thiadiazole-1-oxide (2.9 g; 77%) m.p. 133°–35° C.

$C_{16}H_{20}N_6OS_2$: Found: C, 51.10; H, 5.41; N, 22.32; S, 17.25. Requires: C, 51.04; H, 5.35; N, 22.32; S, 17.03%.

EXAMPLE 17

2-[N-(3-Aminopropyl)-N-(2-thienylmethyl)amino]pyridine (1.5 g) in methanol (20 ml) was added dropwise to a stirred solution of 3,4-dimethoxy-1,2,5-thiadiazole-1-oxide (0.98 g) in methanol (100 ml) maintaining the temperature at 5° C. After 3 hr, a solution of 4-aminomethylpyridine (0.91 g) in methanol (20 ml) was added maintaining the temperature at 5° C. After standing overnight at room temperature a further 0.5 g of 4-aminomethylpyridine in methanol (10 ml) was added and after 3 hr the solvent was evaporated. Chromatography (silica gel, chloroform/methanol, 20:1) and crystallisation from ethanol afforded 3-[3-(N-(2-thienylmethyl)-N-(2-pyridyl)amino)propylamino]-4-[4-pyridylmethyl]amino-1,2,5-thiadiazole-1-oxide (1.04 g; 38%) m.p. 129°–30° C.

$C_{21}H_{23}N_7OS_2$: Found: C, 55.41; H, 5.02; N, 21.33; S, 14.35. Requires: C, 55.61; H, 5.11; N, 21.62; S, 14.14%.

EXAMPLE 18

2-[N-(3-Aminopropyl)-N-(2-thienylmethyl)amino]pyridine (1.45 g) in methanol (40 ml) was added dropwise to a stirred solution of 3,4-dimethoxy-1,2,5-thiadiazole-1,1-dioxide (1.04 g) in methanol (100 ml) maintaining the temperature at 0°–5° C. After 1 hr, anhydrous ammonia was passed through the solution and the mixture left to stand overnight at room temperature. After evaporating the solvent, chromatography (silica gel, chloroform/methanol, 20:1) and crystallisation from ethanol gave 3-[3-(N-2-thienylmethyl-N-(2-pyridyl)amino)propylamino]-4-[4-pyridylmethyl]amino-1,2,5-thiadiazole-1,1-dioxide 1 H₂O, (1.07 g; 46%) m.p. 103°–107° C.

$C_{15}H_{18}N_6O_2S_2$ 1 $H_2O$: Found: C, 45.51; H, 5.14; N, 21.34; S, 16.42. Requires: C, 45.43; H, 5.08; N, 21.20; S, 16.17%.

EXAMPLE 19

2-[N-(3-Aminopropyl)-N-(2-thienylmethyl)amino]pyridine (1.0 g) in methanol (40 ml) was added dropwise to a solution of 3,4-dimethoxy-1,2,5-thiadiazole-1,1-dioxide (0.72 g) in methanol (100 ml) maintaining the temperature at 0°–5° C. After 1 hr, methylamine in ethanol (33% w/w, 0.67 ml) was added and the mixture allowed to stand overnight at room temperature. The solvent was evaporated and the residue chromatographed (silica gel, chloroform/methanol 20:1) to give, after crystallisation from ethanol, 3-[3-(N-2-thienylmethyl-N-(2-pyridyl)amino)propylamino]-4-methylamino-1,2,5-thiadiazole-1,1-dioxide (0.38 g; 24%) m.p. 168°–70° C.

$C_{16}H_{20}N_6O_2S_2$: Found: C, 48.65; H, 5.08; N, 21.52; S, 16.07. Requires: C, 48.96; H, 5.14; N, 21.41; S, 16.34%.

EXAMPLE 20

2-[N-(3-Aminopropyl)-N-benzylamino]pyridine (1.5 g) in methanol (15 ml) was added dropwise to a stirred solution of 3,4-dimethoxy-1,2,5-thiadiazole-1-oxide (1.01 g) in methanol (35 ml) maintaining the temperature at 0°–5° C. After 2.5 hr, 2-aminomethylpyridine (1.01 g) was added and the mixture allowed to stand overnight at room temperature. After evaporating the solvent, chromatography (silica gel, dichloromethane/methanol, 25:1) of the residue and crystallisation from ethanol gave 3-[3-(N-benzyl-N-(2-pyridyl)amino)propylamino]-4-[2-pyridylmethyl]amino-1,2,5-thiadiazole-1-oxide (1.59 g; 57%) m.p. 139°–40° C.

$C_{23}H_{25}N_7OS$: Found: C, 61.78; H, 5.56; N, 21.77; S, 6.99. Requires: C, 61.72; H, 5.63; N, 21.91; S, 7.16%.

EXAMPLE 21

2-[N-(3-Aminopropyl)-N-benzylamino]pyridine (1.5 g) in methanol (15 ml) was added dropwise to a stirred solution of 3,4-dimethoxy-1,2,5-thiadiazole-1-oxide (1.01 g) in methanol (35 ml) maintaining the temperature at 0°–5° C. After 2.5 hr, 3-aminomethylpyridine (1.01 g) was added and the mixture allowed to stand overnight at room temperature. After evaporating the solvent, chromatography (silica gel, dichloromethane/methanol, 25:1) and crystallisation from ethanol/ether gave 3-[3-(N-benzyl-N-(2-pyridyl)amino)propylamino]-4-[3-pyridylmethyl]amino-1,2,5-thiadiazole-1-oxide (0.85 g; 30%) m.p. 114°–116° C.

$C_{23}H_{25}N_7OS$ 0.2 $H_2O$: Found: C, 61,29; H, 5.59; N, 21.72; S, 7.04. Requires: C, 61.23; H, 5.68; N, 21.73; S, 7.11%.

EXAMPLE 22

2-[N-(3-Aminopropyl)-N-benzylamino]pyridine (2.6 g) in methanol (25 ml) was added dropwise to a stirred solution of 3,4-dimethoxy-1,2,5-thiadiazole-1-oxide (1.59 g) in methanol (60 ml) maintaining the temperature at 0°–5° C. After 2.5 hr, 4-aminomethylpyridine (1.59 g) was added and the mixture allowed to stand overnight at room temperature. After evaporating the solvent, chromatography (silica gel, dichloromethane/methanol 25:1) of the residue and crystallisation from ethanol gave 3-[3-(N-benzyl-N-(2-pyridyl)amino)-propylamino]-4-[4-pyridylmethyl]amino-1,2,5-thiadiazole-1-oxide (2.5 g; 57%) m.p. 140°–42° C.

$C_{23}H_{25}N_7OS$ 0.4 $H_2O$: Found: C, 60.91; H, 5.63; N, 21.48; S, 7.15. Requires: C, 60.74; N, 5.71; N, 21.56; S, 7.05%.

EXAMPLE 23

(i) Substituting 3-fluorobenzyl chloride (9.54 g) for 4-fluorobenzyl bromide and using corresponding molar proportions of the reagents in the method of Example 13(i) gave 2-[N-(3-aminopropyl)-N-(3-fluorobenzyl)amino]pyridine (6.64 g) as an oil which was used without further purification.

(ii) Substituting 2-[N-(3-aminopropyl)-N-(3-fluorobenzyl)amino]pyridine (1.5 g) for 2-[N-(3-aminopropyl)-N-(4-fluorobenzyl)amino]pyridine and using corresponding molar proportions of the other reagents in the method of Example 13(ii) gave 3-[3-[N-(3-fluorobenzyl)-N-(2-pyridyl)amino]propylamino]-4-amino-1,2,5-thiadiazole-1-oxide, (0.82 g; 37.4%) m.p. 160°–162° C. (from ethanol).

$C_{17}H_{19}FN_6OS$: Found: C, 54.23; H, 5.10; N, 22.17; S, 8.83. Requires: C, 54.53; H, 5.11; N, 22.45; S, 8.56%.

EXAMPLE 24

(i) Substituting 2-fluorobenzyl chloride (9.54 g) for 4-fluorobenzyl bromide and using corresponding molar proportions of the reagents in the method of Example 13(i) gave 2-[N-(3-aminopropyl)-N-(2-fluorobenzyl)amino]pyridine (9.24 g) as an oil which was used without further purification.

(ii) Substituting 2-[N-(3-aminopropyl)-N-(2-fluorobenzyl)amino]pyridine (1.5 g) for 2-[N-(3-aminopropyl)-N-(4-fluorobenzyl)amino]pyridine and using corresponding molar proportions of the other reagents in the method of Example 13(ii), gave 3-[3-[N-(2-fluorobenzyl)-N-(2-pyridyl)amino]propylamino]-4-amino-1,2,5-thiadiazole-1-oxide, (0.81 g; 37.3%) m.p. 180°–182° C. (from ethanol).

$C_{17}H_{19}FN_6OS$: Found: C, 54.77; H, 5.15; N, 22.22; S, 8.58. Requires: C, 54.53; H, 5.12; N, 22.45; S, 8.56%.

EXAMPLE 25

2-[N-(3-Aminopropyl)-N-(4-fluorobenzyl)amino]-pyridine (1.5 g) in methanol (10 ml) was added dropwise to a stirred solution of 3,4-dimethoxy-1,2,5-thiadiazole-1-oxide (0.95 g) in methanol (100 ml) maintaining the temperature at 0°–5° C. After 3 hrs a solution of 4-aminomethylpyridine (0.94 g) in methanol (10 ml) was added. After a further 3 hrs more 4-aminomethylpyridine (0.46 g) was added and the mixture allowed to stand overnight at room temperature. The solvent was evaporated and the residue chromatographed (silica gel, chloroform/methanol, 20:1) and crystallised from ethanol to give 3-[3-(N-(4-fluorobenzyl)-N-(2-pyridyl)amino)propylamino]-4-[4-pyridylmethyl]amino-1,2,5-thiadiazole-1-oxide, (1.52 g; 56.3%) m.p. 160°–63° C.

$C_{23}H_{24}FN_7OS$: Found: C, 59.47; H, 5.28; N, 21.18; S, 7.10. Requires: C, 59.34; H, 5.20; N, 21.06; S, 6.87%.

EXAMPLE 26

(i) Sodium hydride (1.75 g) was dissolved in dimethylsulphoxide (40 ml) at 70°–75° C. under nitrogen. The solution was cooled to room temperature and 2-(3-aminopropylamino)pyridine (10 g) in dimethylsulphoxide (20 ml) added dropwise with stirring. After 5 minutes, 3-bromomethylthiophene (12.88 g) in dimethylsulphoxide (20 ml) was added dropwise over 45 minutes maintaining the temperature at 25°–35° C. After a further 1.5 hr water (200 ml) was added and the mixture extracted with chloroform. The extract was washed with 2N hydrochloric acid and the pH of the aqueous phase raised to 4. After extracting with chloroform, the pH was raised further to 14 and the solution was extracted with ether. Evaporation of the ether extract gave an oil (10 g) which was further purified by repeating the above extraction procedure but extracting out the impurities at pH 8 with ether. Drying ($K_2CO_3$) and evaporating the final ether extract gave 2-[N-(3-aminopropyl)-N-(3-thienylmethyl)amino]pyridine (8.47 g) as an oil.

(ii) 2-[N-(3-Aminopropyl)-N-(3-thienylmethyl)amino]pyridine (2.47 g) in methanol (25 ml) was added dropwise with stirring to a suspension of 3,4-dimethoxy-1,2,5-thiadiazole-1-oxide (1.62 g) in methanol (60 ml) maintaining the temperature at 0°–5° C. After a further 2 hr, ammonia-saturated methanol (10 ml) was added and the mixture allowed to stand at room temperature overnight. After evaporating the solvent, the residue was chromatographed (silica gel, chloroform/methanol 25:1) and crystallised twice from ethanol/water to give 3-[3-(N-(3-thienylmethyl)-N-(2-pyridyl)amino)propylamino]4-amino-1,2,5-thiadiazole-1-oxide 0.2 $H_2O$, (2.51 g; 69%) m.p. 140°–42° C.

$C_{15}H_{18}N_6OS_2$ 0.2 $H_2O$: Found: C, 49.19; H, 4.94; N, 22.93; S, 17.37. Requires: C, 49.21; H, 5.07; N, 22.96; S, 17.52%.

EXAMPLE 27

2-[N-(3-Aminopropyl)-N-(3-thienylmethyl)amino]-pyridine (2.47 g) in methanol (25 ml) was added dropwise with stirring to a suspension of 3,4-dimethoxy-1,2,5-thiadiazole-1-oxide (1.62 g) in methanol (60 ml) maintaining the temperature at 0°–5° C. After a further 2 hr, a solution of 4-aminomethylpyridine (1.62 g) in methanol (10 ml) was added and the mixture allowed to stand for 3 days at room temperature. After evaporating the solvent, the residue was chromatographed (silica gel, chloroform/methanol 25:1) and crystallised from ethanol/water to give 3-[3-(N-(3-thienylmethyl)-N-(2-pyridyl)amino)propylamino]-4-[4-pyridylmethyl]amino-1,2,5-thiadiazole-1-oxide, (2.57 g; 57%) m.p. 155°–57° C.

C$_{21}$H$_{23}$N$_7$OS$_2$: Found: C, 55.52; H , 5.12; N, 21.68; S, 13.85. Requires: C, 55.61; H, 5.11; N, 21.62; S, 14.14%.

EXAMPLE 28

2-[N-(3-Aminopropyl)-N-benzylamino]pyridine (2.38 g) in methanol (50 ml) was added dropwise to a stirred suspension of 3,4-dimethoxy-1,2,5-thiadiazole-1-oxide (1.62 g) in methanol (20 ml) maintaining the temperature at 0°–5° C. After 3 hr, methylamine in ethanol (33% w/w, 1 ml) was added and the mixture allowed to stand overnight at room temperature. After evaporating the solvent, the residue was chromatographed (silica gel, chloroform/methanol 20:1) and crystallised from ethanol/water to give 3-[3-(N-benzyl-N-(2-pyridyl)amino)propylamino]-4-methylamino-1,2,5-thiadiazole-1-oxide, (1.19 g; 32%) m.p. 122°–23° C.

C$_{18}$H$_{22}$N$_6$OS: Found: C, 58.28; H, 6.11; N, 22.73; S, 8.75. Requires: C, 58.35; H, 5.99; N, 22.69; S, 8.66%.

EXAMPLE 29

(i) Sodium hydride (1.75 g) was dissolved in dimethylsulphoxide (35 ml) at 70°–75° C. under nitrogen. The solution was cooled and 2-(3-aminopropylamino)pyridine (5.0 g) in dimethylsulphoxide (15 ml) added at room temperature. 2-Chloromethylpyridine hydrochloride (5.97 g) in dimethylsulphoxide (15 ml) was added dropwise maintaining the temperature at 25°–35° C. After a further 3 hrs, water (100 ml) was added and the mixture extracted with chloroform. The chloroform extracts were washed with 2N hydrochloric acid and the aqueous layer adjusted to pH 7. After extracting with chloroform, the pH was raised to 14 and extracted again with chloroform. After washing with water and drying (K$_2$CO$_3$), the final chloroform extract was evaporated to give 2-[N-(3-aminopropyl)-N-(2-pyridylmethyl)amino]pyridine (0.83 g) as an oil which was used without further purification.

(ii) To a stirred suspension of 3,4-dimethoxy-1,2,5-thiadiazole-1-oxide (1.76 g) in methanol (60 ml) at 5° C. was added dropwise over 30 minutes 2-[N-(3-aminopropyl)-N-(2-pyridylmethyl)amino]pyridine (2.64 g) in methanol (25 ml). After a further 2 hr at 5°–10° C., anhydrous ammonia was passed through the solution at 5° C. for 30 minutes. The mixture was then stirred for a further 2 hr at room temperature. After evaporating the solvent, the residue was chromatographed (silica gel, chloroform/methanol 20:1) and the fractions which contain the required product were evaporated. The residue was crystallised from ethanol/water to give 3-[3-(N-2-pyridylmethyl-N-(2-pyridyl)amino)-propylamino)-4-amino-1,2,5-thiadiazole-1-oxide 2 H$_2$O, (1.93 g; 49%) m.p. 192°–3° C.

C$_{16}$H$_{19}$N$_7$OS 0.2 H$_2$O: Found: C, 53.40; H, 5.35; N, 26.98; S, 8.97. Requires: C, 53.23; H, 5.42; N, 27.16; S, 8.88%.

EXAMPLE 30

(i) Substituting 3-chloromethylpyridine hydrochloride (10 g) for 2-chloromethylpyridine hydrochloride and using corresponding molar proportions of the reagents in the method of Example 29(i) gave 2-[N-(3-aminopropyl)-N-(3-pyridylmethyl)amino]pyridine (2.81 g) as an oil which was used without further purification.

(ii) Substituting 2-[N-(3-aminopropyl)-N-(3-pyridylmethyl)amino]pyridine (1.18 g) for 2-[N-(3-aminopropyl)-N-(2-pyridylmethyl)amino]pyridine and using corresponding molar proportions of the other reagents in the method of Example 29(ii) gave on recrystallisation from ethanol/water 3-[3-(N-(3-pyridylmethyl)-N-(2-pyridyl)amino)propylamino]-4-amino-1,2,5-thiadiazole-1-oxide, (0.55 g; 25%) m.p. indeterminate.

C$_{16}$H$_{19}$N$_7$OS 0.8 H$_2$O: Found: C, 51.49; H, 5.35; N, 26.45; S, 8.78. Requires: C, 51.68; H, 5.58; N, 26.37; S, 8.62%.

EXAMPLE 31

(i) Substituting 4-chloromethylpyridine hydrochloride (10 g) for 2-chloromethylpyridine hydrochloride and using corresponding molar proportions of the reagents in the method of Example 29(i) gave 2-[N-(3-aminopropyl)-N-(4-pyridylmethyl)amino]pyridine (2.04 g) as an oil which was used without further purification.

(ii) Substituting 2-[N-(3-aminopropyl)-N-(4-pyridylmethyl)amino]pyridine (1.31 g) for 2-[N-(3-aminopropyl)-N-(2-pyridylmethyl)amino]pyridine and using corresponding molar proportions of the other reagents in the method of Example 29(ii) which on recrystallisation from ethanol/water gave 3-[3-(N-(4-pyridylmethyl)-N-(2-pyridyl)amino)propylamino]-4-amino-1,2,5-thiadiazole-1-oxide, (0.84 g; 29%) m.p. 103°–110° C.

C$_{17}$H$_{26}$N$_6$OS 0.4 H$_2$O: Found: C, 55.32; H, 7.38; N, 22.76; S, 8.72. Requires: C, 55.23; H, 7.31; N, 22.73; S, 8.67%.

EXAMPLE 32

(i) A mixture of 1,2-dimethoxycyclobutenedione (0.6 g) and methylamine (33% w/w in ethanol, 0.58 ml) in ether (100 ml) was stirred at room temperature for 3 hr. The precipitate was filtered off and crystallised from methylethylketone to give 1-methylamino-2-methoxycyclobutene-3,4-dione, (0.44 g; 73%).

(ii) Substituting 1-methylamino-2-methoxycyclobutene-3,4-dione (0.94 g) for 1-amino-2-methoxycyclobutenedione and using corresponding molar proportions of the other reagents in the method of Example 12 gave, after crystallisation from dimethylformamide/water, followed by pyridine/water, 1-[3-(N-benzyl-N-(2-pyridyl)amino)propylamino]-2-methylaminocyclobutene-3,4-dione, (0.91 g; 40%) m.p. 226°–228° C.

C$_{20}$H$_{22}$N$_4$O$_2$: Found: C, 68.52; H, 6.25; N, 15.81. Requires: C, 68.55; H, 6.33; N, 15.99%.

EXAMPLE 33

Substituting 2-[N-(2-aminoethyl)-N-benzylamino]pyridine (2.27 g) for 2-[N-(3-aminopropyl)-N-benzylamino] pyridine and using corresponding molar proportions of the other reagents in the method of Example 7 gave on recrystallisation from ethanol/water, 3-[2-(N-benzyl-N-(2-pyridyl)amino)ethylamino]-4-amino-1,2,5-thiadiazole-1-oxide (1.3 g; 36%) m.p. indeterminate.

C$_{16}$H$_{18}$N$_6$OS 1 H$_2$O: Found: C, 53.07; H, 5.58; N, 23.46; S, 8.85. Requires: C, 53.32; H, 5.59; N, 23.32; S, 8.89%.

EXAMPLE 34

(i) Substituting 2-chloromethylfuran (15.0 g) for 2-chloromethylthiophene and using corresponding molar proportions of the other reagents in the method of Example 15(i) gave 2-[N-(3-aminopropyl)-N-(2-furanyl methyl)amino]pyridine (17.07 g) as an oil which was used without further purification.

(ii) Substituting 2-[N-(3-aminopropyl)-N-(2-furanyl methyl)amino]pyridine (2.31 g) for 2-[N-(3-aminopropyl)-N-benzylamino]pyridine and using corresponding molar proportions of the other reagents in the method of Example 7 gave on recrystallisation from ethanol/water 3-[3-(N-(2-furanylmethyl)-N-(2-pyridylamino)propylamino]-4-amino-1,2,5-thiadiazole-1-oxide (0.81 g; 54%) m.p. 114°–6° C.

$C_{15}H_{18}N_6O_2S$: Found: C, 51.86; H, 5.25; N, 24.33; S, 9.54. Requires: C, 52.01; H, 5.24; N, 24.26; S, 9.26%.

EXAMPLE 35

(i) Substituting 2-chloromethylthiazole (10 g) for 2-chloromethylthiophene and using corresponding molar proportions of the other reagents in the method of Example 15(i) gave 2-[N-(3-aminopropyl)-N-(2-thiazolyl methyl)amino]pyridine (5.51 g) as an oil which was used without further purification.

(ii) Substituting 2-[N-(3-aminopropyl)-N-(2-thiazolylmethyl)amino]pyridine (1.5 g) for 2-[N-(3-aminopropyl)-N-benzylamino]pyridine and using corresponding molar proportions of the other reagents in the method of Example 7 gave on recrystallisation from ethanol/water 3-[3-(N-(2-thiazolylmethyl)-N-(2-pyridyl)amino)propylamino]-4-amino-1,2,5-thiadiazole-1-oxide (0.56 g; 28%) m.p. 130°–134° C.

$C_{14}H_{17}N_7O_2S$ 0.75 $H_2O$: Found: C, 44.54; H, 4.73; N, 25.78; S, 17.05. Requires: C, 44.60; H, 4.95; N, 26.01; S, 17.01%.

EXAMPLE 36

(i) Substituting 5-chloro-2-chloromethylthiophene (4.53 g) for 2-chloromethylthiophene and using corresponding molar proportions of the other reagents in the method of Example 15(i) gave 2-[N-(3-aminopropyl)-N-(5-chloro-2-thienylmethyl)amino]pyridine (2.27 g) as an oil which was used without further purification.

(ii) Substituting 2-[N-(3-aminopropyl)-N-(5-chloro-2-thienylmethyl)amino]pyridine (2.23 g) for 2-[N-(3-aminopropyl)-N-benzylamino]pyridine and using corresponding molar proportions of the other reagents in the method of Example 7 gave on recrystallisation from ethanol/water 3-[3-[N-(5-chloro-2-thienylmethyl)-N-(2-pyridyl)amino]propylamino]-4-amino-1,2-5-thiadiazole-1-oxide (1.54 g; 49%) m.p. 96°–100° C.

$C_{15}H_{17}ClN_6OS_2$: Found: C, 45.46; H, 4.31; N, 21.21; Cl, 8.67. Requires: C, 45.39; H, 4.32; N, 21.17; Cl, 8.93%.

EXAMPLE 37

(i) Substituting 4-methoxybenzylchloride (10.8 g) for 2-chloromethylthiophene and using corresponding molar proportions of the other reagents in the method of Example 15(i) gave 2-[N-(3-aminopropyl)-N-(4-methoxybenzyl)amino]pyridine (14.75 g) as an oil which was used without further purification.

(ii) Substituting 2-[N-(3-aminopropyl)-N-(4-methoxybenzyl)amino]pyridine (1.8 g) for 2-[N-(3-aminopropyl)-N-benzylamino]pyridine and using corresponding molar proportions of the other reagents in the method of Example 7 gave on recrystallisation from propan-2-ol 3-[3-[N-(4-methoxybenzyl)-N-(2-pyridyl)amino]propylamino]-4-amino-1,2,5-thiadiazole-1-oxide (1.03 g; 40%) containing 0.5% w/w propan-2-ol m.p. 158°–160° C.

$C_{18}H_{22}N_6O_2S$ 0.06 Pr-2-OH: Found: C, 55.68; H, 5.74; N, 21.44; S, 8.31. Requires: C, 55.96; H, 5.71; N, 21.64; S, 8.26%.

EXAMPLE 38

(i) 2-[N-(3-Aminopropyl)-N-(4-methoxybenzyl)amino]pyridine (4.18 g) in DMSO (16 ml) was added to a solution of sodium methoxide in methanol [prepared from sodium (2.12 g) and methanol (50 ml), and then reducing the volume (4 ml)]. The mixture was heated under reflux for 48 hr. More anhydrous sodium methoxide (0.83 g) was added and the mixture heated for a further 23 hr. The mixture was poured into water and the solution extracted with chloroform. The extract was evaporated at reduced pressure and the residue chromatographed (silica gel, chloroform/methanolic ammonia 20:1) to give 2-[N-(3-aminopropyl)-N-(4-hydroxybenzyl)amino]pyridine (0.57 g) as an oil which was used without further purification.

(ii) Substituting 2-[N-(3-aminopropyl)-N-(4-hydroxybenzyl)amino]pyridine (0.75 g) for 2-[N-(3-aminopropyl)-N-benzylamino]pyridine and using corresponding molar proportions of the other reagents in the method of Example 7 gave on recrystallisation from dimethylformamide/water 3-[3-[N-(4-hydroxybenzyl)-N-(2-pyridyl)amino]propylamino]-4-amino-1,2,5-thiadiazole-1-oxide (0.38 g; 35%) containing 1% w/w dimethylformamide m.p. 187°–189° C.

$C_{17}H_{20}N_6O_2S$ 0.04 DMF 0.2 $H_2O$: Found: C, 54.20; H, 5.49; N, 22.30. Requires: C, 54.23; H, 5.50; N, 22.31%.

EXAMPLE 39

Substituting 2-[N-(3-aminopropyl)-N-(4-fluorobenzyl)amino]pyridine (1.5 g) for 2-[N-(3-aminopropyl-N-(2-thienylmethyl)amino]pyridine and using corresponding molar proportions of reagents in the method of Example 19 gave on recrystallisation from ethanol 3-[3-[N-(4-fluorobenzyl)-N-(2-pyridyl)amino]propylamino]-4-methylamino-1,2,5-thiadiazole-1,1-dioxide (0.89 g; 38%) m.p. 165°–168° C.

$C_{18}H_{21}FN_6O_2S$: Found: C, 53.15; H, 5.23; N, 20.71; S, 7.93. Requires: C, 53.45; H, 5.23; N, 20.78; S, 7.93%.

EXAMPLE 40

Substituting 4-aminoethylpyridine (1.11 g) for 4-aminomethylpyridine and using corresponding molar proportions of the other reagents in the method of Example 17 gave on recrystallisation from ethanol 3-[3-[N-(2-thienylmethyl)-N-(2-pyridyl)amino]propylamino]-4-(4-pyridylethyl)amino-1,2,5-thiadiazole-1-oxide (1.53 g; 54%) m.p. 105°–108° C.

$C_{22}H_{25}N_7OS_2$: Found: C, 56.52; H, 5.44; N, 20.97; S, 13.97. Requires: C, 56.51; H, 5.39; N, 20.97; S, 13.71%.

EXAMPLE 41

Substituting 3,4-dimethoxy-1,2,5,-thiadiazole-1,1-dioxide (1.07 g) for 3,4-dimethoxy-1,2,5-thiadiazole-1-oxide and using corresponding molar proportions of the other reagents in the method of Example 17 gave on recrystallisation from ethanol 3-[3-(N-(2-thienylmethyl)-N-(2-pyridyl)amino]propylamino-4-(4-pyridylmethyl)amino-1,2,5-thiadiazole-1,1 dioxide (1.37 g; 48.6%) m.p. 190°–192° C.

$C_{21}H_{23}N_7O_2S_2$ 1$C_2H_5OH$: Found: C, 53.31; H, 5.73; N, 18.96; S, 12.62. Requires: C, 53.57; H, 5.66; N, 19.01; S, 12.43%.

EXAMPLE 42

Substituting 3,4-dimethoxy-1,2,5-thiadiazole-1, 1-dioxide (1.04 g) for 3,4-dimethoxy-1,2,5-thiadiazole-1-oxide and using corresponding molar proportions of the other reagents in the method in Example 25 gave on recrystallisation from ethanol 3-[3-[N-(4-fluorobenzyl)-N-(2-pyridyl)amino]propylamino]-4-(4-pyridylmethyl- )amino-1,2,5-thiadiazole-1,1-dioxide (1.38 g; 49.5%) m.p. 228°–230° C.

$C_{23}H_{24}FN_7O_2S$: Found: C, 57.16; H, 4.94; N, 20.13; S, 6.9. Requires: C, 57.37; H, 5.02; N, 20.36; S, 6.66%.

EXAMPLE 43

Substituting 2-[N-(3-aminopropyl)-N-(4-fluorobenzyl)amino]pyridine (1.02 g) for 2-[N-(3-aminopropyl)-N-benzylamino]pyridine and using corresponding molar proportions of the other reagents in the method of Example 12 gave on recrystallisation from ethanol 1-amino-2-[3-[N-(4-fluorobenzyl)-N-(2-pyridyl)amino]-propylamino]cyclobutene-3,4-dione (0.6 g; 43%) m.p. 208°–210° C.

$C_{19}H_{19}FN_4O_2$: Found: C, 64.24; H, 5.32; N, 16.05. Requires: C, 64.39; H, 5.40; N, 15.81%.

EXAMPLE 44

Substituting 2-N-(3-aminopropyl)-N-(2-thienylmethyl)amino]pyridine (0.97 g) for 2-[N-(3-aminopropyl)-N-benzylamino]pyridine and using corresponding molar proportions of the other reagents in the method of Example 12 gave on recrystallisation from ethanol 1-amino-2-[3-[N-(2-thienylmethyl)-N-(2-pyridyl-)amino]propylamino]cyclobutene-3,4-dione (0.80 g; 59%) m.p. 227°–229° C.

$C_{17}H_{18}N_4O_2S$: Found: C, 59.62; H, 5.26; N, 16.26; S, 9.66. Requires: C, 59.63; H, 5.30; N, 16.36; S, 9.36%.

EXAMPLE 45

(i) A mixture of 1,2-dimethoxycyclobutenedione (0.5 g) and 4-aminomethylpyridine (0.38 g) in ether (100 ml) was stirred at room temperature for 1 hr. The precipitate was filtered off to give 1-(4-pyridylmethylamino)-2-methoxycyclobutene-3,4-dione (0.46 g) which was used without further purification.

(ii) To a stirred solution of 1-(4-pyridylmethylamino)-2-methoxycyclobutene-3,4-dione (0.3 g) in methanol (100 ml) at 0°–5° C. was added dropwise over 1 hr. 2-[N-(3-aminopropyl)-N-(4-fluorobenzyl)amino]pyridine. The mixture was stirred at room temperature for 1 hr. and then heated under reflux for 1 hr. Addition of water gave a precipitate, which after recrystallisation from methanol/water gave 1-(4-pyridylmethylamino)-2-[3-[N-(4-fluorobenzyl)-N-(2-pyridyl)amino]-propylamino]cyclobutene-3,4-dione (0.17 g; 27.4%) m.p. 198°–201° C.

$C_{25}H_{24}FN_5O_2$: Found: C, 67.46; H, 5.41; N, 15.62. Requires: C, 67.40; H, 5.43; N, 15.72%.

EXAMPLE 46

1,2,-Dimethoxycyclobutene-3,4-dione (0.5 g) and 2-[N-(3-aminopropyl)-N-(2-thienylmethyl)amino]pyridine (0.87 g) were dissolved in the minimum amount of dry ether at 0°–5° C. After 0.5 hr the mixture was warmed to room temperature. After a further 1 hr, 4-aminomethylpyridine in dry ether (20 ml) was added and the mixture heated under reflux for 9 hr. After evaporating the solvent the residue was crystallized from methanol/water and recrystallized from acetonitrile/water to give 1-(4-pyridylmethyl)amino-2-[3-(N-(2-thienylmethyl)-N-(2-pyridyl)amino)propylamino]-cyclobutene-3,4-dione (0.27 g; 17.6%) m.p. 189°–192° C.

$C_{23}H_{23}N_5O_2S$: Found: C, 63.91; H, 5.37; N, 16.12; S, 7.47. Requires: C, 63.72; H, 5.35; N, 16.16; S, 7.40%.

EXAMPLE 47

(i) Substituting 3-aminomethylpyridine (1.26 g) for 4-aminomethylpyridine and using corresponding molar proportions of the other reagents in the method of Example 45(i) gave 1-methoxy-2-(3-pyridylmethylamino)cyclobutene-3,4-dione (1.8 g) as a precipitate which was used without further purification.

(ii) A mixture of 1-methoxy-2-(3-pyridylmethylamino)cyclobutene-3,4-dione (0.88 g) and 2-[N-(3-aminopropyl)-N-(4-fluorobenzyl)amino]pyridine (1.03 g) in methanol (170 ml) was heated under reflux for 1.5 hr. The mixture was cooled and a precipitate formed which after recrystallisation from methanol/water gave 3-[3-(N-(4-fluorobenzyl)-N-(2-pyridyl)amino)-propylamino]-2-(3-pyridylmethylamino)cyclobutene-3,4-dione (0.85 g: 47.2%) m.p. 194°–198° C.

$C_{25}H_{24}FN_5O_2$: Found: C, 67.70; H, 5.41; N, 15.81. Requires: C, 67.40; H, 5.43; N, 15.72%.

EXAMPLE 48

Substituting 2-[N-(3-aminopropyl)-N-(2-thienyl methylamino)pyridine (0.98 g) for 2-[N-(3-aminopropyl)-N-(4-fluorobenzyl)amino]pyridine and using corresponding molar proportions of the other reagents in the method of Example 47(ii) gave on recrystallisation from pyridine/water 1-[3-(N-(2-thienylmethyl)-N-(2-pyridyl-)amino)propylamino]-2-(3-pyridylmethylamino)cyclobutene-3,4-dione (0.62 g; 35.4%) m.p 200°–203° C.

$C_{23}H_{23}N_5O_2S$: Found: C, 63.85; H, 5.30; N, 16.18; S, 7.62. Requires: C, 63.72; H, 5.35; N, 16.16; S, 7.40%.

EXAMPLE 49

Substituting ethylamine in ethanol 33% (0.99 g, 1.3 ml.) for methylamine and using corresponding molar proportions of the other reagents in the method of Example 14 gave on recrystallisation from ethanol 3-[3-[N-(4-fluorobenzyl)-N-(2-pyridyl)amino]propylamino]-4-ethylamino-1,2,5-thiadiazole-1-oxide (0.92 g; 39.4%) m.p. 165°–166° C.

$C_{19}H_{23}FN_6OS$: Found: C, 56.59; H, 5.74; N, 20.85; S, 8.18. Requires: C, 56.70; H, 5.76; N, 20.88; S, 7.97%.

EXAMPLE 50

Substituting n-propylamine (0.43 g; 0.6 ml) in ethanol (5 ml) for methylamine and using corresponding molar proportions of the other reagents in the method of Example 14 gave on recrystallisation from ethanol 3-[3-[N-(4-fluorobenzyl)-N-(2-pyridyl)amino]propylamino]-4-propylamino-1,2,5-thiadiazole-1-oxide (0.46 g; 19%) m.p. 134°–136° C.

$C_{20}H_{25}FN_6OS$: Found: C, 57.50; H, 5.96; N, 20.21. Requires: C, 57.67; H, 6.05; N, 20.18%.

EXAMPLE 51

Substituting 2-propylamine (0.43 g; 0.48 ml) in ethanol (5 ml) for methylamine and using corresponding molar proportions of the other reagents in the method of Example 14 gave on recrystallisation from ethanol/water 3-[3-[N-(4-fluorobenzyl)-N-(2-pyridyl)amino]-propylamino]-4-prop-2-ylamino-1,2,5-thiadiazole-1-oxide (0.5 g; 21%) m.p. 150°–151° C.

$C_{20}H_{25}FN_6OS$: Found: C, 57.52; H, 6.10; N, 20.05. Requires: C, 57.67; H, 6.05; N, 20.18%.

I claim:

1. A compound of formula (1):

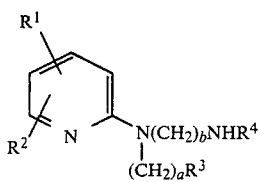 (1)

or a pharmaceutically acceptable salt thereof, where
  $R^1$ and $R^2$ are the same or different and are hydrogen, $C_{1-6}$ alkyl, $C_{1-6}$ alkoxy or halogen;
  $R^3$ is optionally substituted phenyl or optionally substituted pyridyl, where the optional substituent is one $C_{1-6}$ alkyl, $C_{1-6}$ alkoxy, or hydroxy group or halogen atom; or optionally substituted thiazolyl, optionally substituted furanyl or optionally substituted thienyl where the optional substituent is one $C_{1-6}$ alkyl or $C_{1-6}$ alkoxy group or halogen atom;
  a is from 1 to 6
  b is from 2 to 4
and $R^4$ is a group of formula (2):

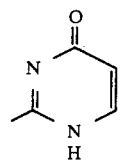 (2)

2. A compound according to claim 1 where $R^1$ and $R^2$ are both hydrogen.

3. A compound according to claim 1 where a is 1.

4. A compound according to claim 1 where b is 3.

5. A compound according to claim 1 where $R^3$ is phenyl, 2-chlorophenyl, 2-fluorophenyl, 3-chlorophenyl, 3-fluorophenyl, 4-chlorophenyl, 4-fluorophenyl, 2-thienyl, 3-thienyl, 2-furanyl, 2-thiazolyl, 2-pyridyl, 3-pyridyl or 4-pyridyl.

6. A compound according to claim 5 where $R^3$ is phenyl, 4-fluorophenyl, 2-thienyl or 3-thienyl.

7. A pharmaceutical composition having histamine $H_1$-antagonist activity comprising an effective amount of a compound according to claim 1 and a pharmaceutically acceptable carrier.

8. A method of blocking histamine $H_1$-receptors which comprises administering to a subject an effective amount to block said receptors of a compound according to claim 1.

* * * * *